(12) United States Patent
Hollingsworth

(10) Patent No.: US 6,235,930 B1
(45) Date of Patent: May 22, 2001

(54) PROCESS FOR THE PREPARATION OF 3,4-DIHYDROXYBUTANOIC ACID AND DERIVATIVES THEREOF FROM SUBSTITUTED PENTOSE SUGARS

(75) Inventor: Rawle I. Hollingsworth, Haslett, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/282,779

(22) Filed: Mar. 31, 1999

(51) Int. Cl.$^7$ .................................................. C07C 51/00
(52) U.S. Cl. .................. 562/515; 562/579; 562/587; 549/295; 549/429; 568/853
(58) Field of Search .................. 549/295, 429; 562/515, 579, 587; 568/853

(56) References Cited

U.S. PATENT DOCUMENTS

| | | |
|---|---|---|
| 4,994,597 | 2/1991 | Inoue et al. . |
| 5,087,751 | 2/1992 | Inoue et al. . |
| 5,292,939 | 3/1994 | Hollingsworth . |
| 5,319,110 | 6/1994 | Hollingsworth . |
| 5,374,773 | 12/1994 | Hollingsworth . |
| 5,998,633 | * 12/1999 | Jacks et al. ................. 549/313 |
| 6,069,270 | * 5/2000 | Nohira et al. ............... 562/401 |
| 6,077,964 | * 6/2000 | Tuck et al. .................. 549/295 |

FOREIGN PATENT DOCUMENTS

0513430 * 11/1992 (EP) .

OTHER PUBLICATIONS

Lindstrom et al, Alkai and Oxygen–Alkali Treatment of 4–Deoxy–2,3–hexodiulose and 3–Deoxy–erythro–pentose, Aceta Chem. Scand., Ser. B Jun. (1977), B31(6), p. 479–89, .*
E.J. Corey et al., 1978 J. Amer. Chem. Soc. 100:1942–1943.
H. Hayashi et al., J. Amer. Chem. Soc. 95:8749–8757 (1973).
Y. Mori et al., Tetrahedron Letts. 29:5419–5422 (1988).
H.M. Shieh et al., Tetrahedron Letts. 23:4643–4646 (1982).
Uchikawa et al., Bull. Chem. Soc. Jpn. 61:2025–2029 (1988).

* cited by examiner

Primary Examiner—Gary Geist
Assistant Examiner—Taylor V. Oh
(74) Attorney, Agent, or Firm—Ian C. McLeod

(57) ABSTRACT

A process for the preparation of 3,4-dihydroxybutanoic acid (I) and 3-hydroxy-γ-butyrolactone (V) thereof from a 3-leaving group substituted pentose source is described. In particular, the process relates to the synthesis of (R)-3,4-dihydroxybutanoic acid and (R)-3-hydroxy-γ-butyrolactone from a 3-leaving group substituted L-pentose sugars. The process uses a base and a peroxide to convert the pentose source to the chiral 3,4-dihydroxybutanoic acid compound. The chiral 3,4-dihydroxybutanoic acid can be further converted to 3-hydroxy-γ-butyrolactone by acidification. The chiral compound is useful as a chemical intermediate to the synthesis of various drugs and other products.

18 Claims, 3 Drawing Sheets

PROCESS FOR THE PREPARATION OF 3,4-DIHYDROXYBUTANOIC ACID AND DERIVATIVES THEREOF FROM SUBSTITUTED PENTOSE SUGARS

STATEMENT REGARDING FEDERALLY SPONSORED RESEARCH OR DEVELOPMENT

None.

CROSS-REFERENCE TO RELATED APPLICATIONS

None.

BACKGROUND OF THE INVENTION (1) Field of the Invention

The present invention relates to a process for the preparation of 3,4-dihydroxybutanoic acid and 3-hydroxy-γ-butyrolactone therefrom starting with a pentose sugar source substituted in the 3-position, preferably in the chiral form. In particular, the process relates to the synthesis of (R)-3,4-dihydroxybutanoic acid and (R) 3-hydroxy-γ-butyrolactone from a substituted L-pentose source. The process uses a base and a peroxide to convert the pentose source to chiral 3,4-dihydroxybutanoic acid. The chiral 3,4-dihydroxybutanoic acid can be further converted to 3-hydroxy-γ-butyrolactone by acidification. The products are useful to the synthesis of various drugs and natural products.

(2) Description of Related Art

The current art on the oxidation of carbohydrates to 3,4-dihydroxybutanoic acid and derivatives describe the transformation of substituted hexoses which are usually only of the D-configuration which upon conversion yield only the 3,4-dihydroxybutanoic acid and derivatives in the (S)-configuration. In these reactions, chiral 3,4-dihydroxybutanoic acid and derivatives thereof are synthesized from carbohydrates by oxidation of 4-substituted hexoses with hydrogen peroxide. The chiral carbon atom is derived from the 5-position of the hexose sugar. Because most naturally occurring hexose sugars are of the D-configuration, this method is good only for preparation of (S)-3,4-dihydroxybutanoic acid and derivatives. In contrast to the position with hexose sugars, some pentose sugars such as xylose and arabinose occur in considerable amounts in the L-configuration.

There are methods for transforming 3,4-dihydroxybutanoic acid and derivatives to important molecules such as carnitine, however the process is extremely problematic starting from the (S)-derivatives because the stereochemistry at the 3-position has to be inverted. The prior art describes chemical and enzymatic processes for the preparation of the (S)-3,4-dihydroxybutanoic acid and derivatives by oxidation of sugars, but not for the preparation of (R)-3,4-dihydroxybutanoic acid and derivatives.

U.S. Pat. Nos. 4,994,597 and 5,087,751 to K. Inoue et al disclose methods for making optically active 3,4-dihydroxybutyric acid derivatives by reacting R-3-chloro-1,2-propanediol made by stereo selective microorganism decomposition of racemic 3-chloro-1,2-propanediol.

U.S. Pat. No. 5,319,110 to R. Hollingsworth discloses a process for synthesis of an internal cyclic ester such as a lactone by converting a hexose source, which contains hexose as a substituent and another sugar attached to the hexose substituent in the 4 position via (S)-3,4-dihydroxybutanoic acid as an intermediate. U.S. Pat. No. 5,374,773 to R. Hollingsworth discloses a process for the synthesis (S)-3,4-hydroxybutanoic salt by converting a hexose source which contains hexose as a substituent and another sugar attached to the hexose substituent in the 4 position via (S)-3,4-dihydroxybutyric acid as an intermediate. U.S. Pat. No. 5,292,939 to R. Hollingsworth discloses synthesis of (S)-3,4-dihydroxybutyric acid from substituted D-hexose.

(S)-3,4-dihydroxybutyric acid and derivatives, such as (S)-1,2,4 butanetriol that is formed by its reduction, are important 4-carbon compounds that are pivotal intermediates in the synthesis of various drugs and other natural products. These include the preparation of compounds such as eicosanoids (E. J. Corey et al. 1978. J. Amer. Chem. Soc. 100: 1942–1943), modified nucleic acid bases (H. Hayashi et al. 1973. J. Amer. Chem. Soc. 95: 8749–8757), the polyol function of macrolide antibiotics (Y. Mori et al. 1988. Tetrahedron Letts. 29: 5419–5422), and (−) aplysistatin, an anticancer agent (H. M. Shieh and G. D. Prestwich. 1982. Tetrahedraon Letts. 23: 4643–4646).

A common route to the (S)-3-hydroxy-γ-butyric acid or butyrolactone equivalent used in the above synthesis involves the use of malic acid as the chiral raw material. This is reduced to a triol and the two vicinal hydroxyl groups protected by acetylization with acetone and an acid catalyst. The remaining primary hydroxyl group is then oxidized to an aldehyde or acid and the acetal group is then removed. Preparation of (R) and (S) isomers of gamma-lactone from (R) or (S) malic acid has also been described by Uchikawa et al. 1988. Bull. Chem. Soc. Jpn. 61: 2025–2029. These routes have been of academic interest because malic acid is reasonably expensive and two groups have to be reduced to the level of an alcohol and one then selectively oxidized. (S)-3-hydroxy-γ-butyrolactone as a synthetic intermediate in the drug industry is a very expensive material.

Therefore, it is desirable to develop a process for transforming pentose sugars such as xylose and arabinose into useful building blocks for the preparation of chiral compounds for use in the drug, agri-chemical and advanced material science industries. In particular, it is desired that a method for oxidizing pentoses which would remove a 1 carbon from the reducing end and an oxygen from the 2-position give either the (R) or (S) isomer of 3,4-dihydroxybutanoic acid and derivatives, using essentially the same reaction and depending on whether the D or L pentose is used.

SUMMARY OF THE INVENTION

The present invention provides a process for oxidizing a precursor compound which is a pentose, a furanose or a pentanal by removing a carbon from the reducing end and an oxygen from the 2-position which produces either the (R) or (S) isomer of 3,4-dihydroxybutanoic acid and derivatives. The process uses essentially the same reaction conditions to produce either the (R) or (S) isomer of 3,4-dihydroxybutanoic acid and derivatives depending on whether a D or L pentose is used as the starting material. In particular, the invention provides a method for preparing 3,4-dihydroxybutanoic acid from a pentose, furanose, or pentanal in a reaction mixture comprising a peroxide in the presence of a base. Further, the invention provides 3-hydroxy-γ-butyrolactone by treating 3,4-dihydroxybutanoic acid with an acid in the presence of heat.

Objects

It is therefore an object of the present invention to provide a process for preparing a chiral 3,4-dihydroxybutanoic acid preferably in a chiral form from a pentose, furanose, or pentanal source. It is further an object of the present invention to provide a process which is simple, economical and inexpensive. These and other objects will become increasingly apparent by reference to the following description and the drawings.

DESCRIPTION OF THE DRAWINGS

FIG. 8A shows the structure of a 3,4-O-isopropylidene pentose. FIG. 8B shows the structure for a 2,3-O-isopropylidene pentose. FIG. 8C shows the structure for a 3,5-O-benzylidene furanose.

DETAILED DESCRIPTION OF THE INVENTION

Figure 1:
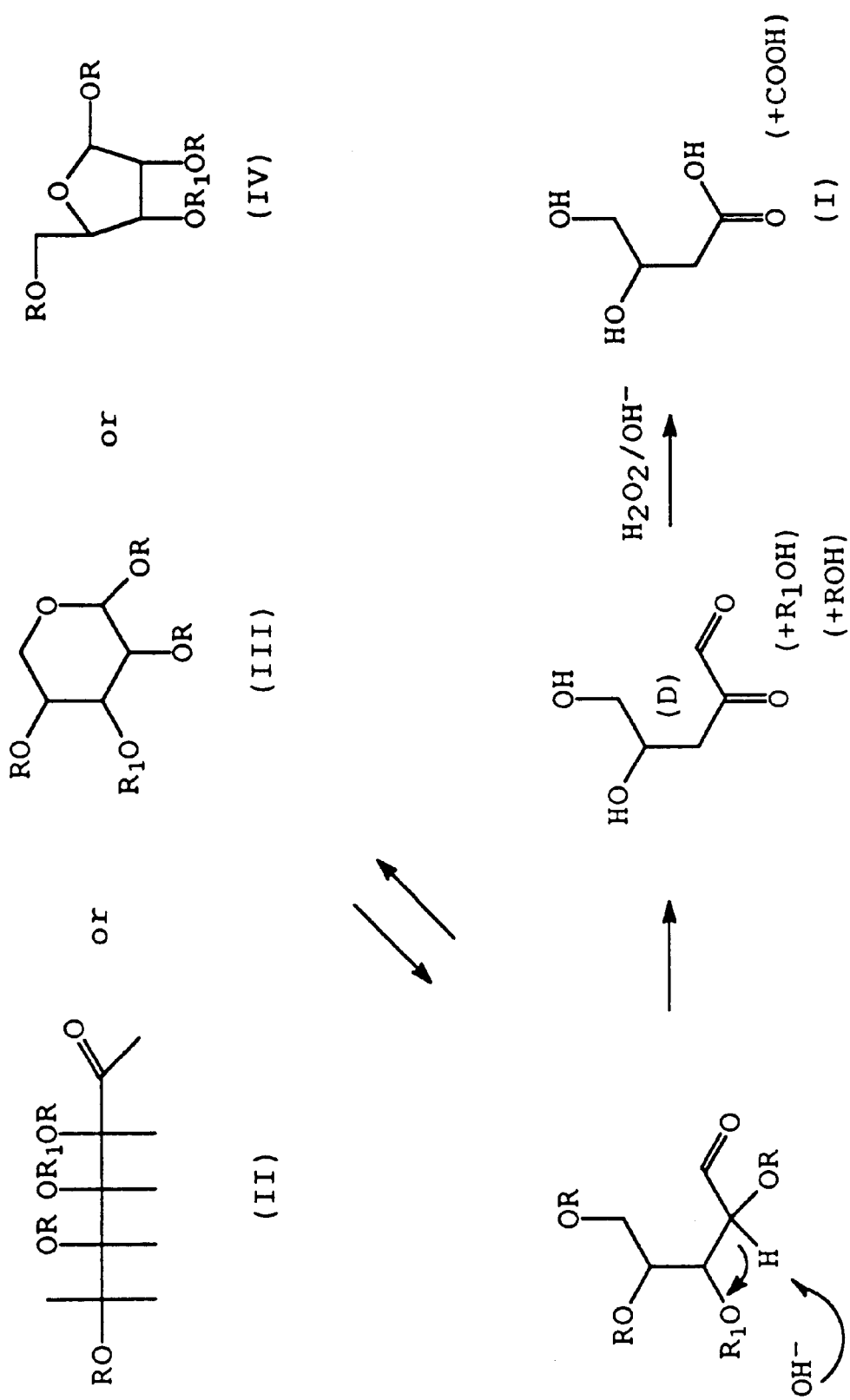
FIG. 1 shows the conversion of a pentose sugar substituted at the 3-position (R1) to chiral 3,4-dihydroxybutanoic acid (I). Compound (II) is a substituted pentanal, compound (III) is a substituted pyranose, and compound (IV) is a substituted furanose.

In particular, the present invention relates to a process for the preparation of 3,4-dihydroxybutanoic acid (I) which comprises: reacting a mixture of a 3-leaving group substituted precursor compound selected from the group consisting of a pentose, a furanose and a pentanal of the formulas, for the pentose

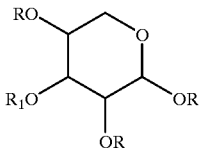

for the furanose

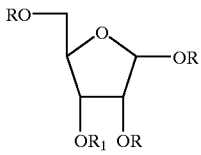

for the pentanal

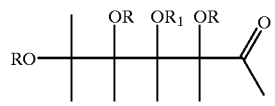

wherein $R_1$ is a protecting leaving group and wherein R is optionally H or a protecting leaving group with a solvent containing a peroxide in the presence of a base to produce (I) and a protonated leaving group; and separating (I) from the mixture. R in the 1, 2, 4, or 5 positions can be any combination of groups which includes but is not limited to the group consisting of hydroxy, alkyloxy, aryloxy, acyloxy, halo, sulfonyloxy, sulfate, phosphate. When R is not a hydroxy group, the R is defined herein as a protecting group and the position it occupies is protected. The 3-leaving group ($R_1$) can be any group which includes but is not limited to alkyloxy, aryloxy, acyloxy, halo, sulfonyloxy, sulfate, phosphate.

The present invention particularly relates to a process for the conversion of a pentose source containing a pentose substituted at the 3-position to chiral 3,4-dihydroxybutanoic acid and derivatives. The process consists of the oxidation of either an L or D pentose sugar, which causes the removal of the 1-carbon, giving either the (R) or (S) isomer of 3,4-dihydroxybutanoic acid under essentially the same reaction conditions. Thus, oxidation of the L pentose will give rise to the (R) isomer and oxidation of the D pentose will give rise to the (S) isomer.

In particular, the present invention relates to a process for the preparation of 3,4-dihydroxybutanoic acid (I) which comprises: reacting a mixture of a 3-leaving group substituted-n-pentanal selected from the group consisting of 2,4,5-trihydroxy-3-leaving group substituted-n-pentanal, 2,4-dihydroxy-3-leaving group 4-O-protected substituted-n-pentanal, 2-hydroxy-3-leaving group 4,5-di-O-protected substituted-n-pentanal, 4-hydroxy-3-leaving group 2,5-di-O-protected substituted-n-pentanal, 5-hydroxy-3-leaving group 2,4-di-O-protected substituted-n-pentanal, and 3-leaving group 2,4,5-tri-O-protected substituted-n-pentanal with a solvent containing a peroxide in the presence of a base to produce (I) and a protonated leaving group, and then separating (I) from the mixture.

In this process, (I) can be produced by providing a 3-leaving group substituted pentose selected from the group consisting of 2,4,5-trihydroxy-3-$R_1$-O-pentose, 2,4-protected-3-$R_1$-O-pentose, 4-protected-3-$R_1$-O-pentose, 2-protected-3-$R_1$-O-pentose, and 5-protected-3-$R_1$-O-pentose in the mixture wherein $R_1$ is the leaving group and protected is the protecting group R. In particular embodiments of the invention, the 3-leaving group pentose can be a 3-leaving group substituted furanose (IV) or a 3-leaving group substituted pyranose (III).

Thus, in one particular embodiment of the invention, the 3-leaving group substituted furanose (IV) is selected from the group consisting of 2,5-dihydroxy-3-leaving group substituted furanose, 5-protected-2-hydroxy-3-leaving group substituted furanose, 2-protected-5-hydroxy-3-leaving group substituted furanose, and a 2,5-protected-3-leaving group substituted furanose in the mixture.

In another particular embodiment of the invention, the substituted pyranose (III) is selected from the group consisting of 2,4-dihydroxy-3-leaving group substituted pyranose, 2-O-protected-4-hydroxy-3-leaving group substituted pyranose, 4-O-protected-2-hydroxy-3-leaving group substituted pyranose, and a 2,4-O-protected-3-leaving group substituted pyranose in the mixture. In a preferred embodiment of the invention (I), (III), (IV) and (V) are each a single chiral compound.

The present invention further relates to a process for the preparation of 3-hydroxy-γ-butyrolactone (V) which comprises: reacting a mixture of a 3-leaving group substituted precursor compound selected from the group consisting of a pentose, a furanose and a pentanal of the formulas, for the pentose

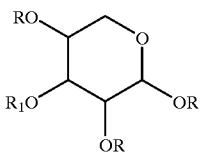

for the furanose

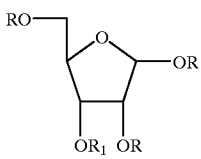

for the pentanal

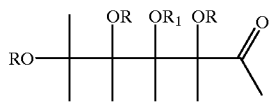

wherein $R_1$ is a protecting leaving group and wherein R is optionally H or a protecting leaving group with a solvent containing a peroxide in the presence of a base to produce (I) and a protonated leaving group; and treating the (I) with an acid and heat to form the 3-hydroxy-γ-butyrolactone (V).

In particular, the present invention relates to a process for the preparation of 3-hydroxy-γ-butyrolactone (V) which comprises: reacting a mixture of a 3-leaving group substituted precursor compound selected from the group consisting of 2,4,5-trihydroxy-3-leaving group substituted-n-pentanal, 2,4-dihydroxy-3-leaving group 4-O-protected substituted-n-pentanal, 2-hydroxy-3-leaving group 4,5-di-O-protected substituted-n-pentanal, 4-hydroxy-3-leaving group 2,5-di-O-protected substituted-n-pentanal, 5-hydroxy-3-leaving group 2,4-di-O-protected substituted-n-pentanal, and 3-leaving group 2,4,5-tri-O-protected substituted-n-pentanal with a solvent containing a peroxide in the presence of a base to produce (I) and a protonated leaving group, then treating the (I) with an acid and heat to form the 3-hydroxy-γ-butyrolactone(V).

In this process, (V) can be produced by providing a 3-leaving group substituted pentose selected from the group consisting of 2,4,5-trihydroxy-3-$R_1$-O-pentose, 2,4-protected-3-R-O-pentose, 4-protected-3-$R_1$-O-pentose, 2-protected-3-$R_1$-O-pentose, and 5-protected-3-$R_1$-O-pentose in the mixture wherein $R_1$ is the leaving group and protected is the protecting group R. In particular embodiments of the invention, the 3-leaving group pentose can be a 3-leaving group substituted furanose (IV) or a 3-leaving group substituted pyranose (III).

Thus, in one particular embodiment of the invention, the 3-leaving group substituted furanose (IV) is selected from the group consisting of 2,5-dihydroxy-3-leaving group substituted furanose, 5-protected-2-hydroxy-3-leaving group substituted furanose, 2-protected-5-hydroxy-3-leaving group substituted furanose, and a 2,5-protected-3-leaving group substituted furanose in the mixture.

In another particular embodiment of the invention, the substituted pyranose (III) is selected from the group consisting of 2,4-dihydroxy-3-leaving group substituted pyranose, 2-O-protected-4-hydroxy-3-leaving group substituted pyranose, 4-O-protected-2-hydroxy-3-leaving group substituted pyranose, and a 2,4-O-protected-3-leaving group substituted pyranose in the mixture. In a preferred embodiment of the invention (I), (III), (IV) and (V) are each a single chiral compound. In a preferred embodiment of the invention (I), (III), (IV) and (V) are each a single chiral compound.

The present invention further relates to a process for the preparation of unsaturated lactone (VI) which comprises: reacting a mixture of a 2,4,5-O-R 3-leaving group substituted compound selected from the group consisting of a pentose, a furanose and a pentanal with a solvent containing peroxide and a base to produce 3,4-dihydroxybutanoic acid (I) and a protonated leaving group; treating the (I) with an acid and heat to form the 3-hydroxy-γ-butyrolactone (V); and distilling under reduced pressure in the presence of the acid to produce the unsaturated lactone (VI).

In particular, the present invention relates to a process for the preparation of unsaturated lactone (VI) which comprises: reacting a mixture of a 3-leaving group substituted-n-pentanal selected from the group consisting of 2,4,5-trihydroxy-3-leaving group substituted-n-pentanal, 2,4-dihydroxy-3-leaving group 4-O-protected substituted-n-pentanal, 2-hydroxy-3-leaving group 4,5-di-O-protected substituted-n-pentanal, 4-hydroxy-3-leaving group 2,5-di-O-protected substituted-n-pentanal, 5-hydroxy-3-leaving group 2,4-di-O-protected substituted-n-pentanal, and 3-leaving group 2,4,5-tri-O-protected substituted-n-pentanal with a solvent containing a peroxide in the presence of a base to produce (I) and a protonated leaving group, treating the (I) with an acid and heat to form the 3-hydroxy-γ-butyrolactone (V); and then distilling under reduced pressure in the presence of the acid to produce the unsaturated lactone (VI). In this process, (VI) can be produced by providing a 3-leaving group substituted pentose such as 3-leaving group substituted furanose (IV) or 3-leaving group substituted pyranose (III), selected from the group consisting of 2,4,5-trihydroxy-3-R-O-pentose, 2,4-protected-3-R-O-pentose, 4-protected-3-R-O-pentose, 2-protected-3-R-O-pentose, and 5-protected-3-R-O-pentose in the mixture where R is the leaving group. In one embodiment of the process, the 3-leaving group substituted furanose (IV) is selected from the group consisting of 2,5-dihydroxy-3-leaving group substituted furanose, 5-protected-2-hydroxy-3-leaving group substituted furanose, 2-protected-5-hydroxy-3-leaving group substituted furanose, and a 2,5-protected-3-leaving group substituted furanose in the mixture. In another embodiment of the process, the substituted pyranose (III) is selected from the group consisting of 2,4,5-trihydroxy-3-leaving group substituted pyranose, 2,5-O-protected-3,4-dihydroxy-3-leaving group substituted pyranose, 4,5-O-protected-2,3-dihydroxy-3-leaving group substituted pyranose, and a 2,4-O-protected-3,5-dihydroxy-3-leaving group substituted pyranose in the mixture.

Figure 8A:
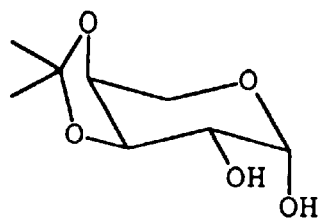
FIGS. 8A to 8C show structures of various alkylidene or arylidene substituted pentoses.
Figure 8B:
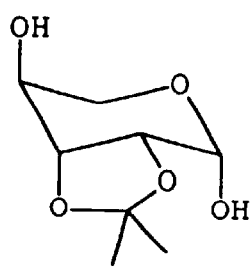
Figure 8C:
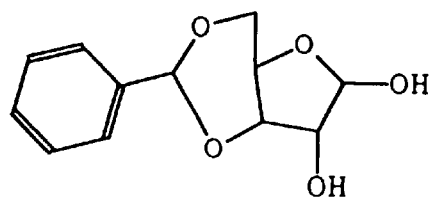

In the preferred process of the present invention, the pentose is selected from the group consisting of D and L isomers. Examples of pentoses that can be used are arabinose, ribulose, xylose and lyxose. In particular, the pentose can be a 3-leaving group substituted pentose with a saccharide as the leaving group. In a preferred embodiment, the pentose is selected from the wherein the pentose is selected from the group consisting of 3-O-methyl pentose, 3-O-alkyl-pentose, 3,4-O-alkylidene-pentose, 3,5-O-alkylidene-pentose, 2,3-O-alkylidene-pentose, 3,4-O-arylidene-pentose, 3,5-O-arylidene-pentose, 2,3-O-arylidene-pentose, 3-O-acyl-pentose, 3,4-O-acylidene-pentose, 2,3-O-acylidene-pentose, 3,5-O-acylidene-pentose, ester-substituted-pentoses and 3-O-sugar substituted-pentose wherein the sugar provides the leaving group. In a particular embodiment the pentose is selected from the group consisting of 3,4-O-isopropylidene-pentose, 2,3-O-isopropylidene-pentose, and 3,5-O-benzylidene-pentose. FIGS. 8A and 8B are examples of 3,4-O-isopropylidene and 2,3-O-isopropylidene substituted pentoses, and FIG. 8C is an example of 3,5-O-benzylidene substituted pentose.

Furthermore, in the process of the present invention the 3-leaving group is selected from the group consisting of alkyloxy, aryloxy, acyloxy, halo, sulfonyloxy, sulfate, phosphate, and a saccharide and wherein (I), (III) and (IV) are each a single chiral compound. In a preferred embodiment, (I) is an (R) isomer or an (S) isomer and the pentose is selected from the group consisting of 3-O-methyl-arabinose, 3,4-O-methyl-arabinose, 3,4-O-isopropylidene-arabinose, 3-O-galactopyranosyl-arabinose, and 2,3-O-isopropylidene-arabinose. In a most preferred embodiment the 2,4,5-trihydroxy-3-substituted-n-pentanal or other substituted pyranose or furanose is a D-sugar or a L-sugar.

In performing the process of the present invention, the peroxide is selected from the group consisting of hydrogen peroxide, alkaline earth peroxides, and combinations thereof, and the base is selected from the group consisting of alkaline earths, alkaline metals, substituted ammonium hydroxides and combinations thereof. The selection of the peroxide and the base is well within the skill of the art. In performing the process, the solvent is selected from the group consisting of water and water miscible organic solvents, methanol, isopropanol, dioxane, tetrahydrofuran (THF), dimethylformamide and combinations thereof. In a preferred embodiment of the process, the peroxide is hydrogen peroxide and the base is sodium hydroxide.

Preferably the sodium hydroxide or potassium hydroxide molar concentration is between 1 to 2 fold of the total 3-leaving group substituted pentose. The 3-leaving group substituted pentose source is preferably at least 0.05 percent up to 80% by weight per volume of the reaction mixture. Preferably the reaction of the base with the 3-leaving group substituted pentose source is conducted for at least 4 hours and preferably between about 10 and 24 hours. The reaction is conducted at a preferred temperature between 25° C. and 80° C. The base is between about 0.005 M and 0.2 M, wherein the hydrogen peroxide is between about 0.05 M and 0.2 M and wherein the 3-leaving group substituted pentose is at least about 0.05 percent by weight per volume of the reaction mixture.

Therefore, according to the present invention, pentose sugars can be converted to chiral 3,4-dihydroxybutanoic acid by oxidation with a peroxide source and a base if the pentose sugar is substituted with a leaving group at the 3-position. FIG. 1 shows the conversion of a 3-leaving group substituted pyranose or furanose to 3,4-dihydroxybutanoic acid. The reaction proceeds by oxidation with a peroxide source and a base. As long as the 3-position is substituted with a leaving group, the substituted sugar is converted to 3,4-dihydroxybutanoic acid. In FIG. 1, R in the 1, 2, 4, or 5 positions is can be any combination of groups which includes but is not limited to the group consisting of hydroxy, alkyloxy, aryloxy, acyloxy, halo, sulfonyloxy, sulfate, phosphate. When R is not a hydroxy group it is defined as a protecting group and the position it occupies is protected. The 3-leaving group R$_1$ can be any group which includes but is not limited to alkyloxy, aryloxy, acyloxy, halo, sulfonyloxy, sulfate, phosphate.

While the nature of the 3-leaving group is quite variable, the most easily obtained functionality is an alkoxy group.

Hence 3-O-methyl pentoses are good substrates as are certain acetals such as 3,4-O-isopropylidene, 2,3-O-isopropylidene and 3,5-O-benzylidene pentose acetals (FIGS. 8A, 8B and 8C, respectively). Acyl and other ester substitutions and disaccharides such as 3-O-β-D-galactopyranosyl-D-arabinose are also useful substrates. Thus, in addition to pentoses having 3-leaving groups, pentoses having 3,4-leaving groups, 2,3-leaving groups and 3,5-leaving groups are all encompassed by the present invention.

Figure 2:
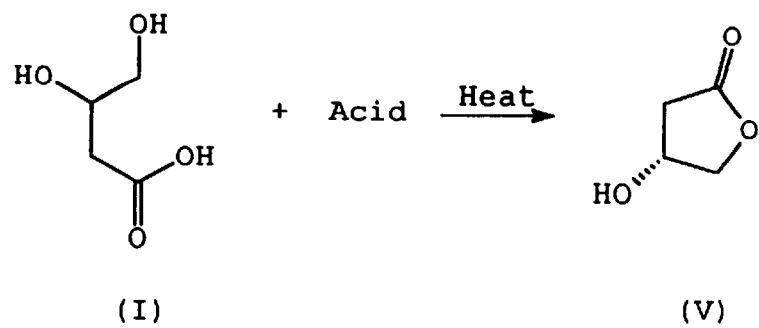
FIG. 2 shows the conversion of chiral 3,4-dihydroxybutanoic acid (I) to 3-hydroxy-γ-butyrolactone (V) (gamma-lactone).

The dihydroxybutyric acid can be converted to the corresponding 3-hydroxy-γ-butyrolactone (gamma-lactone) by acidification with a mineral acid, concentrating and then extracting the product into an organic solvent such as ethyl acetate, chloroform, dimethylformamide, or tetrahydrofuran (THF) as shown in FIG. 2. Gamma-lactone can be dehydrated, on heating in the presence of acid and under reduced pressure to yield the unsaturated lactone (2(5H)-furanone). Treatment of the gamma-lactone with hydrogen bromide in acetic acid in the presence of ethanol will readily yield (R)-4-bromo-3-hydroxybutanoic acid ethyl ester, a key fragment in chiral 3-hydroxy fatty acid synthesis.

The preferred reactions are shown in schemes I, II and III as follows:

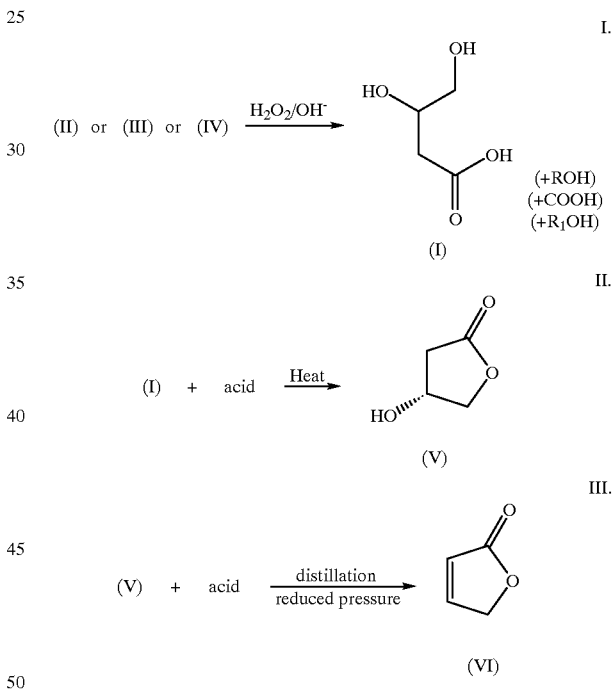

Scission of the bond between the two carbonyl groups of D (FIG. 1) resulting from the degradation of the 3-leaving group substituted pentose source occurs in the presence of alkaline hydrogen peroxide before any competing reactions to yield 3,4-dihydroxybutanoic acid (I) which is stable to further reaction. On acidification of the reaction mixture, (I) undergoes spontaneous cyclization to yield gamma-lactone, 3-hydroxy-γ-butyrolactone (V). The gamma-lactone can be converted to the unsaturated lactone (VI) by distillation of the acidic reaction mixture under reduced pressure.

3,4-dihydroxybutanoic acid (I), HCOOH, R$_1$OH and ROH were the only products formed from the 3-leaving group substituted pentose such as arabinose when treated with alkaline hydrogen peroxide at 65° C. for 10 hours. Acidification of the reaction mixture and concentration to dryness led to complete conversion of the 3,4- hydroxybutanoic acid to the gamma lactone. This could be isolated by chromatography on silica gel or converted to the unsaturated lactone by distillation of the acidic mixture under reduced pressure.

It is to be understood that the chirality of any of the 3,4-hydroxybutanoic acid (I), gamma-lactone (V) and unsaturated lactone (VI) products is dependant on the chirality of the 3-leaving group substituted pentose. For example a 3-leaving group substituted L-pentose will yield only (R) 3,4-hydroxybutanoic acid (I), gamma-lactone (V), or unsubstituted lactone (VI), whereas a 3-leaving group substituted D-pentose will yield only (S) 3,4-hydroxybutanoic acid (I), gamma-lactone (V), or unsubstituted lactone, 2(5H)-furanone (VI).

The process of the present invention opens the way to the preparation, in high yield, of large quantities of valuable chiral building blocks from a cheap, renewable, natural resource. These chiral building blocks can be used in the pharmaceutical, chemical, and polymer industries and reduce dependence on petrochemicals.

The following examples are intended to promote a further understanding of the present invention.

EXAMPLE 1

Figure 3:
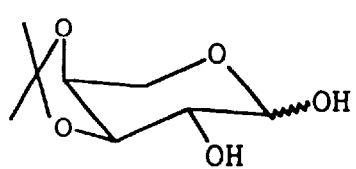
FIG. 3 shows the structure for 3,4-O-isopropylidene-L-arabinose.
Figure 4:
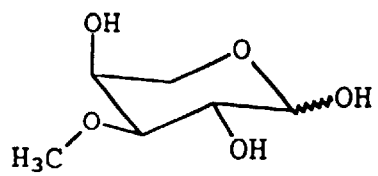
FIG. 4 shows the structure for 3-O-methyl-L-arabinose.

This example was performed to demonstrate the conversion of 3,4-O-isopropylidene-L-arabinose (FIG. 3) to (R)-3,4-dihydroxybutanoic acid and then (R)-3-hydroxy-γ-butyrolactone (gamma-lactone) using hydrogen peroxide and sodium hydroxide according to the process of the present invention.

3,4-O-isopropylidene-L-arabinose (30 grams) was treated with 2700 ml of 0.36% sodium hydroxide and 27 grams of 30% hydrogen peroxide. The mixture was heated at 65° C. for 10 hours to form the 3,4-dihydroxybutanoic acid. Afterwards, the 3,4-dihydroxybutanoic acid was extracted with one volume of ethyl acetate and concentrated to a syrup.

To form the gamma-lactone, the 3,4-dihydroxybutanoic acid formed above and concentrated to a syrup was acidified to pH 1 with 6 M sulfuric acid, and the acidified syrup concentrated at 40° C. until no more solvent was removed. Then the syrup was extracted with 1.5 liters of ethyl acetate. The ethyl acetate layer was concentrated to yield 15.5 grams (96%) of (R)-3-hydroxy-γ-butyrolactone. The product was greater than 90% pure as judged by gas chromatography. Chiral GC analysis on a cyclodextrin phase showed that there was greater than 99.8% of the (R)-3-hydroxy-γ-butyrolactone product.

EXAMPLE 2

This example was performed to demonstrate the conversion of 3,4-O-isopropylidene-L-arabinose to (R)-3,4-dihydroxybutanoic acid and then (R)-3-hydroxy-γ-butyrolactone (gamma-lactone) using hydrogen peroxide and sodium hydroxide according to a modification of the process of the present invention.

The oxidation was carried out on 60 grams of 3,4-O-isopropylidene-D-arabinose as in Example 1 except that the volumes of the liquids were considerably reduced but the desired concentration of the hydrogen peroxide and sodium hydroxide were maintained by pumping in the solutions. Therefore, the acetal which was dissolved in 800 ml of water and the sodium hydroxide (40 grams) which was dissolved in 300 ml of water and the hydrogen peroxide (60 grams) which was dissolved in 300 ml of water were added to the solution heated at 56° C. over a 6 hour period. After addition of the solutions was completed, the heating was continued for a further three hours. Then the 3,4-dihydroxybutanoic acid was isolated as described in Example 1. The yield and purity was similar.

The (R)-3-hydroxy-γ-butyrolactone product was prepared from the 3,4-dihydroxybutanoic acid as described in Example 1. The yield and purity was similar.

EXAMPLE 3

Figure 6:
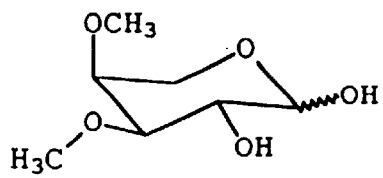
FIG. 6 shows the structure for 3,4-O-methyl-L-arabinose.

This example was performed to demonstrate the conversion of 3,4-O-methyl-L-arabinose (FIG. 6) to (R)-3,4-dihydroxybutanoic acid and then (R)-3-hydroxy-γ-butyrolactone (gamma-lactone) using hydrogen peroxide and sodium hydroxide according to the process of the present invention.

3,4-O-methyl-L-arabinose (30 grams) was treated with 2700 ml of 0.36% sodium hydroxide and 27 grams of 30% hydrogen peroxide. The mixture was heated at 65° C. for 10 hours. Afterwards, the 3,4-dihydroxybutanoic acid was extracted with one volume of ethyl acetate and concentrated to a syrup.

To form the gamma-lactone, the 3,4-dihydroxybutanoic acid formed above and concentrated to a syrup was acidified to pH 1 with 6 M sulfuric acid, and the acidified syrup concentrated at 40° C. until no more solvent was removed. Then the syrup was extracted with 1.5 liters of ethyl acetate. The ethyl acetate layer was concentrated to yield 95% (R)-3-hydroxy-γ-butyrolactone. The product was greater than 95% pure as judged by gas. chromatography. The optical purity was greater than 99.8%.

EXAMPLE 4

Figure 5:
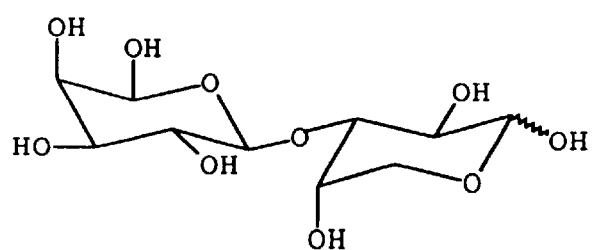
FIG. 5 shows the structure of 3-O-β-D-galactopyranoysl-D-arabinose.

This example was performed to demonstrate the conversion of 3-O-β-D-galactopyranosyl-D-arabinose (FIG. 5) to (S)-3,4-dihydroxybutanoic acid and then (S)-3-hydroxy-γ-butyrolactone (gamma-lactone) using hydrogen peroxide and sodium hydroxide according to the process of the present invention.

3-O-β-D-galactopyranosyl-D-arabinose (30 grams) was treated with 2700 ml of 0.36% sodium hydroxide and 27 grams of 30% hydrogen peroxide. The mixture was heated at 65° C. for 10 hours. Afterwards, the 3,4-dihydroxybutanoic acid was extracted with one volume of ethyl acetate and concentrated to a syrup.

To form the gamma-lactone, the 3,4-dihydroxybutanoic acid formed above and concentrated to a syrup was acidified to pH 1 with 6 M sulfuric acid, and the acidified syrup concentrated at 40° C. until no more solvent was removed. Then the syrup was extracted with 1.5 liters of ethyl acetate. The ethyl acetate layer was concentrated to yield 85% (R)-3-hydroxy-γ-butyrolactone. The product was greater than 90% pure as judged by gas chromatography. The optical purity was greater than 99.8%.

EXAMPLE 5

Figure 7:
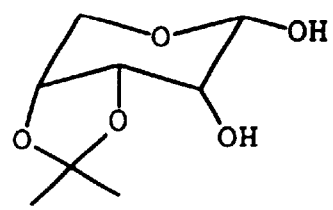
FIG. 7 shows the structure of 3,4-O-isopropylidene-D-arabinose.

This example was performed to demonstrate the conversion of 3,4-O-isopropylidene-D-arabinose (FIG. 7) to (S)-3,4-dihydroxybutanoic acid and then to (S)-3-hydroxy-γ-butyrolactone (gamma-lactone) using hydrogen peroxide and sodium hydroxide according to the process of the present invention.

2,3-O-isopropylidene-D-arabinose (30 grams) was treated with 2700 ml of 0.36% sodium hydroxide and 27 grams of 30% hydrogen peroxide. The mixture was heated at 65° C. for 10 hours. Afterwards, the 3,4-dihydroxybutanoic acid was extracted with one volume of ethyl acetate and concentrated to a syrup.

To form the gamma-lactone, the 3,4-dihydroxybutanoic acid formed above and concentrated to a syrup was acidified to pH 1 with 6 M sulfuric acid, and the acidified syrup concentrated at 40° C. until no more solvent was removed. Then the syrup was extracted with 1.5 liters of ethyl acetate. The ethyl acetate layer was concentrated to yield 60% (S)-3-hydroxy-γ-butyrolactone. The product was greater than 85% pure as judged by gas chromatography. The optical purity was greater than 99.8%.

EXAMPLE 6

Unsaturated lactone (2(5H)-furanone) is prepared from 3-hydroxy-γ-butyrolactone (gamma-lactone). After acidification and concentration of the gamma-lactone synthesized according to any one of Examples 1, 2, 3, 4, or 5, it is subjected to distillation under reduced pressure to yield a liquid that boils at 60° C. (25 mm Hg) which contains glycolic acid and water. A later fraction is collected at a bath temperature of 160° C. which is redistilled to give 2(5H)-furanone. Optionally, the product can be redistilled to remove any residual gamma-lactone.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A process for the preparation of 3,4-dihydroxybutanoic acid (I) which comprises:

(a) reacting a mixture of a 3-leaving group substituted precursor compound selected from the group consisting of a pentose, a furanose and a pentanal of the formulas, for the pentose

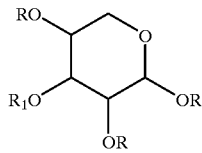

for the furanose

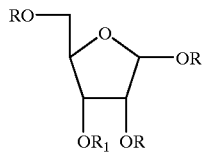

for the pentanal

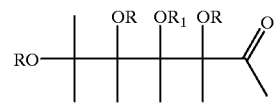

wherein $R_1$ is a protecting leaving group and wherein R is optionally H or a protecting leaving group with a solvent containing a peroxide in the presence of a base to produce (I); and (b) separating the (I) from the mixture.

2. The process of claim 1 wherein the 3,4-dihydroxybutanoic acid is produced by providing a substituted pentose as the compound selected from the group consisting of 2,4,5-trihydroxy-3-leaving group substituted-n-pentanal, 2,4-dihydroxy-3-leaving group 4-O-protected substituted-n-pentanal, 2-hydroxy-3-leaving group 4,5-di-O-protected substituted-n-pentanal, 4-hydroxy-3-leaving group 2,5-di-O-protected substituted-n-pentanal, 5-hydroxy-3-leaving group 2,4-di-O-protected substituted-n-pentanal, and 3-leaving group 2,4,5-tri-O-protected substituted-n-pentanal.

3. The process of claim 2 wherein the pentose is selected from the group consisting of 3-O-methyl pentose, 3-O-alkyl-pentose, 3,4-O-alkylidene-pentose, 3,5-O-alkylidene-pentose, 2,3-O-alkylidene-pentose, 3,4-O-arylidene-pentose, 3,5-O-arylidene-pentose, 2,3-O-arylidene-pentose, 3-O-acyl-pentose, 3,4-O-acylidene-pentose, 2,3-O-acylidene-pentose, 3,5-O-acylidene-pentose, ester-substituted-pentoses and 3-O-sugar substituted-pentose wherein the sugar provides the leaving group.

4. The process of claim 2 wherein the substituted pentose is selected from the group consisting of 3,4-O-isopropylidene-pentose, 2,3-O-isopropylidene-pentose, and 3,5-O-benzylidene-pentose.

5. The process of claim 2 wherein the 3-leaving group substituted pentose is selected from the group consisting of D and L isomers.

6. The process of claim 2 wherein the 3-leaving group substituted pentose is selected from the group consisting of 3-O-methyl-arabinose, 3,4-O-esthyl-arabinose, 3,4-O-isopropylidene-arabinose, 3-O-galactopyranosyl-arabinose, and 2,3-O-isopropylidene-arabinose.

7. The process of claim 1 wherein the 3-leaving group substituted compound is a 3-leaving group substituted furanose.

8. The process of claim 7 wherein the 3-leaving group substituted furanose is selected from the group consisting of 2,5-dihydroxy-3-leaving group substituted furanose, 5-O-protected-2-hydroxy-3-leaving group substituted furanose, 2-O-protected-5-hydroxy-3-leaving group substituted furanose, and a 2,5-O-protected-3-leaving group substituted furanose.

9. The process of claim 1 wherein the 3-leaving group substituted compound is a 3-leaving group substituted pyranose.

10. The process of claim 9 wherein the 3-leaving group substituted pyranose is selected from the group consisting of 2,4-dihydroxy-3-leaving group substituted pyranose, 2-O-protected-4-hydroxy-3-leaving group substituted pyranose, 4-O-protected-2-hydroxy-3-leaving group substituted pyranose, and 2,4-O-protected-3-leaving group substituted pyranose in the mixture.

11. The process of any one of claim 1, 2, 7, or 9 wherein the 3,4-dihydroxybutanoic acid is a single chiral compound.

12. The process of any one of claims 1, 2, 7, or 9 wherein the peroxide is selected from the group consisting of hydrogen peroxide, alkaline earth peroxides, and combinations thereof and wherein the base is selected from the group consisting of alkaline earths, alkaline metals, substituted ammonium hydroxides and combinations thereof.

13. The process of any one of claims 1, 2, 7, or 9 wherein the peroxide is hydrogen peroxide and the base is sodium hydroxide.

14. The process of any one of claims 1, 2, 7, or 9 wherein the solvent is selected from the group consisting of water, methanol, isopropanol, dioxane, tetrahydrofuran (THF), dimethylformamide and combinations thereof.

15. The process of any one of claims 1, 2, 7, or 9 wherein the leaving group is selected from the group consisting of alkyloxy, aryloxy, acyloxy, halo, sulfonyloxy, sulfate, phosphate, and saccharide.

16. The process of any one of claims 1, 2, 7, or 9 wherein the leaving group is selected from the group consisting of acyl, alkyloxy, aryloxy, acyloxy, halo, sulfonyloxy, sulfate, phosphate, and a saccharide, and wherein the 3,4-dihydroxybutanoic acid is a single chiral compound.

17. The process of any one of claims 1, 2, 7, or 9 wherein the 3,4-dihydroxybutanoic acid is an R isomer or an S isomer.

18. The process of any one of claims 1, 2, 7, or 9 wherein the 3-leaving group substituted-n-pentanal is a D-sugar or a L-sugar.

\* \* \* \* \*

UNITED STATES PATENT AND TRADEMARK OFFICE
CERTIFICATE OF CORRECTION

PATENT NO. : 6,235,930 B1
DATED : May 22, 2001
INVENTOR(S) : Rawle I. Hollingsworth Page 1 of 1

It is certified that error appears in the above-identified patent and that said Letters Patent is hereby corrected as shown below:

Column 5,
Line 50, "3-R-O-pentose" should be --3,$R_1$-O-pentose --.

Column 6,
Lines 61 and 62, "wherein the pentose is selected from" should be deleted.

Column 7,
Line 58, "is" after "positions" and before "can" should be deleted.

Column 12,
Line 40, "3, 4-O-esthyl-arabinose" should be -- 3,4-O-methyl-arabinose --.

Signed and Sealed this

Twenty-fifth Day of June, 2002

Attest:

Attesting Officer

JAMES E. ROGAN
*Director of the United States Patent and Trademark Office*